(12) United States Patent
Lizotte (10) Patent No.: US 7,372,632 B2
(45) Date of Patent: May 13, 2008

(54) APPARATUS AND METHODS FOR THE INSPECTION OF MICROVIAS IN PRINTED CIRCUIT BOARDS

(75) Inventor: Todd E. Lizotte, Hooksett, NH (US)

(73) Assignee: Hitachi Via Mechanics, Ltd., Ebina-shi, Kanagawa (JP)

( * ) Notice: Subject to any disclaimer, the term of this patent is extended or adjusted under 35 U.S.C. 154(b) by 56 days.

(21) Appl. No.: 11/517,924

(22) Filed: Sep. 7, 2006

(65) Prior Publication Data

US 2008/0074749 A1 Mar. 27, 2008

(51) Int. Cl.
*G02B 27/10* (2006.01)
*G06K 9/00* (2006.01)
*H04N 9/47* (2006.01)
*G01N 21/00* (2006.01)

(52) U.S. Cl. .......... 359/626; 382/145; 382/147; 348/126; 348/131; 356/237.5

(58) Field of Classification Search ........... 250/559.05, 250/559.06, 559.34, 559.42; 219/121.7; 348/126, 131; 356/237.5, 619, 626; 382/145, 382/147
See application file for complete search history.

(56) References Cited

U.S. PATENT DOCUMENTS

| | | | | |
|---|---|---|---|---|
| 6,697,154 B2* | 2/2004 | Owen et al. | ............. | 356/237.5 |
| 7,203,355 B2* | 4/2007 | Levi et al. | .................. | 382/145 |
| 2005/0190959 A1* | 9/2005 | Kohler et al. | ................ | 382/147 |

* cited by examiner

*Primary Examiner*—David N. Spector
(74) *Attorney, Agent, or Firm*—Davis Bujold & Daniels, P.L.L.C.

(57) ABSTRACT

An imaging method and imaging system for inspecting features located at a known inter-feature pitch on portions of a target surface. The system includes a lens array having a plurality of lenses wherein the lenses of the lens array have an inter-lens pitch and an inter-field of view pitch corresponding to the inter-feature pitch, and an array of imaging elements having an inter-element pitch corresponding to the inter-feature pitch, whereby the imaging system images only field of view areas of the target surface containing features.

12 Claims, 14 Drawing Sheets

APPARATUS AND METHODS FOR THE INSPECTION OF MICROVIAS IN PRINTED CIRCUIT BOARDS

FIELD OF THE INVENTION

The present invention relates to a method and apparatus for the scanning and imaging of features of interest on printed circuit boards and, more particularly, to a method and apparatus for image inspection of vias of a printed circuit board using imaging lens arrays and time delay and integration processing.

BACKGROUND OF THE INVENTION

The manufacture of high density microelectronic packages and devices, such as integrated chip packages (ICPs) or printed circuit boards for cell phones, requires the fabrication of single or multilayer printed circuit boards (PCBs) having high density arrays of small holes referred to as microvias. Microvias are formed using sophisticated mechanical and laser drilling systems and, once formed are plated to provide electrical connections and leads to and between the layers, circuits and circuit elements of single and multi-layer PCBs.

Over the last several years the number of microvias that can be and are formed into a single layer or a single or multi-layer PCB has increased dramatically and it is now conceivable to have several hundreds of thousands of microvias in a single layer of a PCB used to manufacture ICPs. Since microvias provide the electrical or communication link or links to each layer or level of a PCB or multi-layer PCB it is critical that these small holes are processed and fabricated correctly to fulfil their intended purposes and functions. The fabrication of vias, however, is subject to numerous potential defects, such as missed holes, blocked or partially drilled holes, over or under sized or mis-shapen holes, liftoff, fracture or failure of the printed circuit pads surrounding the vias, often due to the ablation of pads by the microvia hole drilling process, and the presence of organic and other residues or smears on the pads due to inadequate de-smearing and cleaning processes, including residues or smears of transparent substances that are very difficult to detect.

The inspection of single or multi-layer PCBs, and in particular the inspection of microvia holes and microvias at various points in the fabrication process is therefore critical to the fabrication of PCBs and ICPs. The inspection of vias is typically automated and several illumination and inspection techniques using flood illumination and automated camera frame grabbers and analysis software have been employed to inspect these partially drilled microvias, typically <100 μm (~0.004") in diameter and with aspect ratios of 1:1 to 1:3, hole diameter to depth, by imaging and analyzing successive fields of view across the PCB.

Figure 1A:
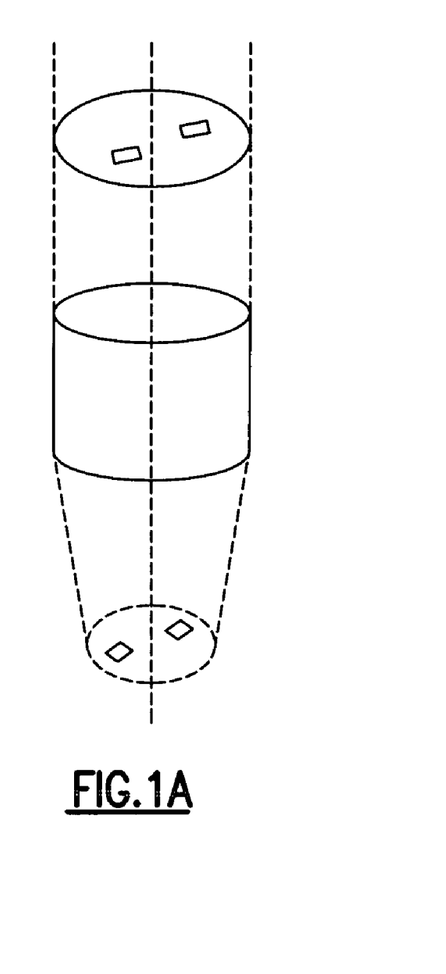
FIGS. 1A and 1B are diagrammatic illustrations of problems of the prior art.
Figure 1B:
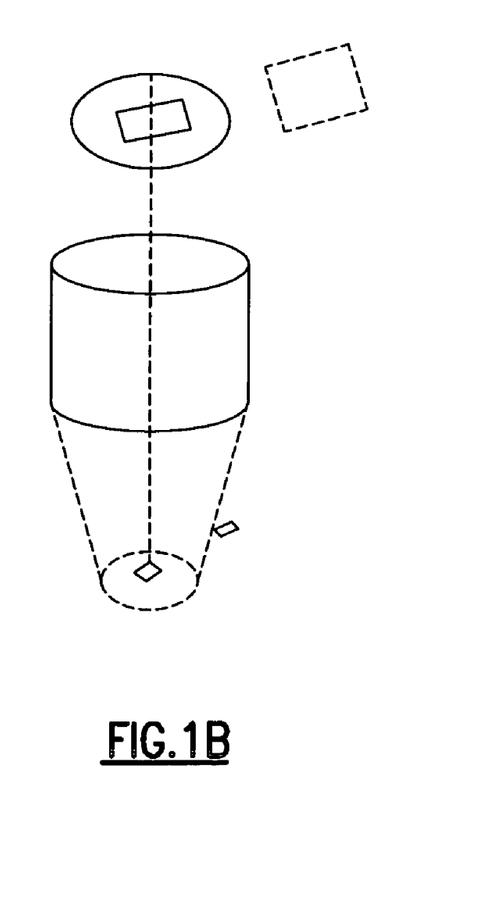

The methods of the prior art, however, inherently provide only low magnification of the fields of view, however, resulting in a relatively low number of image pixels in each image and a lack of resolution as regards any features, such as microvias or portions of microvias, appearing in an image. To illustrate, and as shown in FIGS. 1A and 1B, the methods of the prior art could only image one field of view over the entire array of pixels for the camera. The magnification and image resolution of the system is limited by the separation between the features being inspected, since the single field of view magnifies both the features of interest and increases the separation between the features shown in the image. The choice is thereby between an imaging system such as illustrated in FIG. 1A that images a larger field of view, that is, a larger area of a PCB, but at a lower resolution, or an imaging system such as illustrated in FIG. 1B that has higher magnification to resolve smaller features but at the cost of a correspondingly smaller field of view that often will not include all of the features of interest. The ability of the methods of the prior art to detect flaws and problems of various types is thereby limited, because pitch separation increases with magnification. The limits on image resolution in turn result in a significant possibility that defects, sometimes a majority of the actual defects, are not detected, which in turn results in unacceptable or undesirably low yields from the fabrication process.

Another problem with the methods of the prior art, and in particular scanning systems having wide fields of view and using retro-reflected laser illumination together with fluorescence emission or flood illumination, is that a large part of the illumination energy and the subsequent image scanning process is expended on relatively large areas that do not include microvias. The illumination and scanning of areas that are, in fact, not of interest thereby undesirably wastes a significant part of the system energy emission and processing throughput.

It must also be noted with regard to these problems of the prior art that these methods of the prior art are not readily scalable, so that these problems of the prior art become rapidly more severe as the microvias are reduced in size and as higher and higher microvia and circuit densities are achieved in PCBs.

To illustrate, current AOI systems cannot be increased in resolution, that is, cannot use higher image magnification, because the resulting increase in image processing load would unacceptably reduce the inspection throughput of the systems. The effective decrease in image feature resolution per pixel, however, is significantly decreased as the microvias become smaller and smaller, that is, each pixel represents a proportionally larger portion of the microvia image as the sizes of the microvias is reduced. The decrease in image resolution with decreasing microvia size, however, proportionally decreases the probability that a given feature of a microvia, such as a fault or a contaminating object or objects, can or will be adequately represented and detected in the image. For example, since the field of view of the imaging mechanism is fixed, a reduction in microvia size from 0.65 μm to 0.25 μm results in a reduction of more than half in the pixel resolution of the image. Since defects on the order of 2 μm can be problematic, the current systems of the prior art will thereby fail to achieve the required level of quality control necessary to ensure high yields on such products as chip packages which utilize <+25 micron diameter microvias.

This problem will continue to become more and more severe as PCBs Boards become denser and denser with potential microvias densities of >300 k per panel layer and forseeable densities approaching 500 k microvias per panel.

The present invention provides solutions to these and other problems of the prior art.

SUMMARY OF THE INVENTION

The present invention is directed to an imaging method and imaging system for inspecting features located at a known inter-feature pitch on portions of a target surface. The system includes a lens array having a plurality of lenses wherein the lenses of the lens array have an inter-lens pitch and an inter-field of view pitch corresponding to the inter-feature pitch, and an array of imaging elements having an inter-element pitch corresponding to the inter-feature pitch, whereby the imaging system images only field of view areas of the target surface containing features.

The system of the present invention may also include an illumination transformation element located between the lens array and the imaging element array for transforming reflected imaging radiation from the field of view areas of the target surface into visible light for imaging by the imaging elements.

The system may further include a filtering element located between the lens array and the imaging array to limit wavelengths of at least one of reflected imaging radiation reflected from the target surface and radiation emitted by the illumination transformation element in transforming the reflected imaging radiation from the target surface.

The system of the present invention may further include an image transformation optical element for modifying the characteristics of an image represented by the reflected imaging radiation from the target surface.

The system may yet further include an illumination element for generating illumination radiation for illuminating the field of view areas of the target surface, and a radiation redirection element located between the imaging array and lens array to receive the illumination radiation from the illumination element and direct the illumination radiation to the target surface and to pass reflected imaging radiation from the target surface to the imaging array.

Certain embodiments of the present invention may instead include a plurality of illumination elements for generating illumination radiation corresponding wavelengths for illuminating the field of view areas of the target surface, and a plurality of radiation redirection elements located between the imaging array and lens array, each radiation redirection element receiving the illumination radiation from at least one corresponding illumination element and directing the received illumination radiation to the target surface and passing reflected imaging radiation of a corresponding wavelength from the target surface to the imaging array.

In still further embodiment, the lens and imaging element arrays may be two dimensional arrays imaging a corresponding two dimensional array of viewing areas of the target surface, or the lens array may be a two dimensional array of rows of lenses wherein each row of lenses contains lenses of a single magnification and successive rows of lenses contain lenses of different magnifications and the lens array is selectively indexed by rows row to select a single row of lenses as a linear array of lenses at a corresponding magnification for imaging of the features.

In yet further embodiments, the system may include optical cross-talk baffles located between optical paths between the viewing areas and the imaging element array. The cross-talk baffles may, for example, take the form of ring trenches surrounding each lense of the lens arrays or slits in a radiation redirection element between optical paths between the lenses of the lens array and the array of imaging elements.

BRIEF DESCRIPTION OF THE DRAWINGS

The invention will be described in greater detail with reference to the drawings, wherein.

DETAILED DESCRIPTION OF THE PREFERRED EMBODIMENTS

As will be described in the following, the present invention concerns a system and method providing an increased pixel resolution over the diameter of the microvias while, at the same time, increasing the inspection processing throughput. A system of the present is configurable, for example, as either a linear two dimensional (2D) imaging Charge Coupled Device (CCD) camera or as two dimensional (2D) CCD array camera to image microvias or blind hole vias in either a continuous scan process or in a "step and repeat" process. The system and method of the present invention may also be used to image and inspect conductor traces or through hole via interconnects within multi-layer printed circuit board assemblies (PCBs) as are commonly used within the high density printed circuit board industry.

The following descriptions will focus, however, on the inspection of microvias and the detection of defects, such as partially drilled microvias, as presenting the most difficult inspection task. As will be described, the method of the present invention employs lens array imaging wherein micro lenses are fabricated into a row or array to act as individual microscope objectives, each having its own field of view and imaging that field of view to a specific section of a CCD imaging camera.

According to the present invention, and as illustrated in FIGS. 2A, 2B, 2C and 2D, for example, the imaging systems 10 of the present invention employ linear or two dimensional arrays 12 of individual lenses 14 wherein each of the individual lenses 14 of a lens array 12 magnifies the features 16, such as one or more microvias or features of a microvia located on a target surface 16T, such as a PCB, and in a corresponding field of view 18. In the illustrated embodiments, the pitch 20L of the lens array, that is, the pitch between adjacent lenses 14 of the lens array 12, is matched to the known or anticipated pitch 20F of the features 16 to be imaged. This construction thereby allows the pitch 20L of the lenses 14 to remain constant while allowing magnification of only the features 16 of interest. This method thereby images only an array 22 of viewing areas 18 that are located at a pitch separation 20F corresponding to the pitch separation 20L of the lenses 14 and the anticipated pitch separation 20F of the features 16 to be imaged. As illustrated in FIGS. 2A-2D, the images 24 of each lens 14 of a lens array 12 are imaged onto corresponding imaging elements 26 of, for example, an imaging element array 28 wherein the imaging elements 26 of the camera device 30 may, for example, be Charge Coupled Devices (CCDS) arranged with an imaging element pitch 20E corresponding to that of the lenses 14 and thus to that of the viewing areas 18 and the features 16 appearing in the viewing areas 18.

This method thereby allows more features 16 to be imaged and measured over the total viewing area of the imaging element array 28 by imaging only the viewing areas 18 of actual interest, which in total are typically significantly less than the total possible viewing area of a PCB. FIG. 2D, for example, is an illustration of a scanning camera system 10 that would scan over the fields of view 18 of a square lens array 12 to inspect an entire chip package microvia array.

In this regard, it must be noted that high density packaging typically uses a fixed pitch grid pattern for microvia interconnects, using, for example, standardized pitch separations of 150 µm, 300 µm, 600 µm, and that such packaging is typically standardized and is manufactured in high volumes. It is therefore economically feasible and cost effective to construct a lens array 12 and imaging element array 28 for each of a wide variety of package designs, including odd pitch geometries or patterns.

Figure 2A:
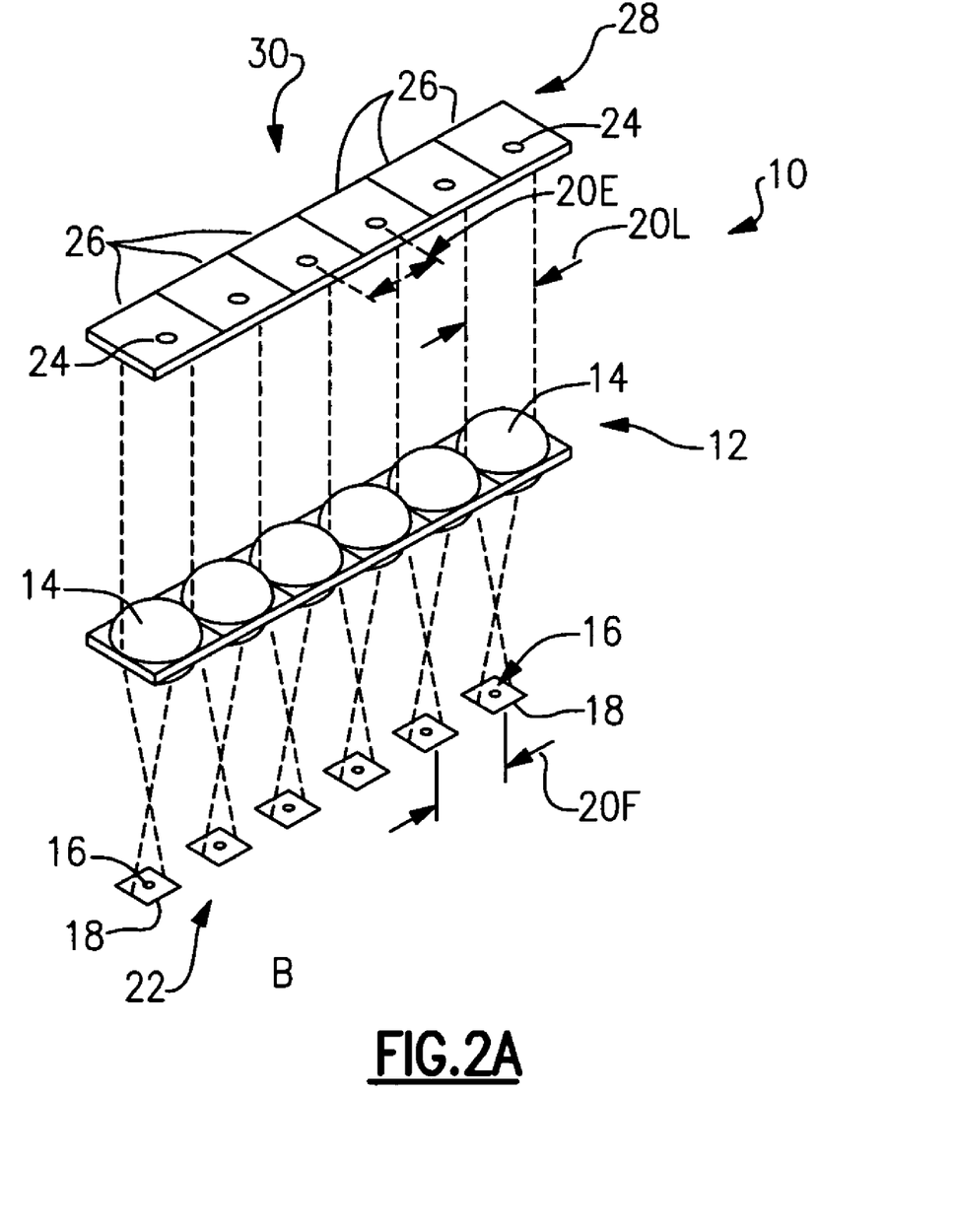
FIGS. 2A-2D are diagrammatic representations of implementations of lens arrays and camera imaging elements of the present invention.
Figure 2B:
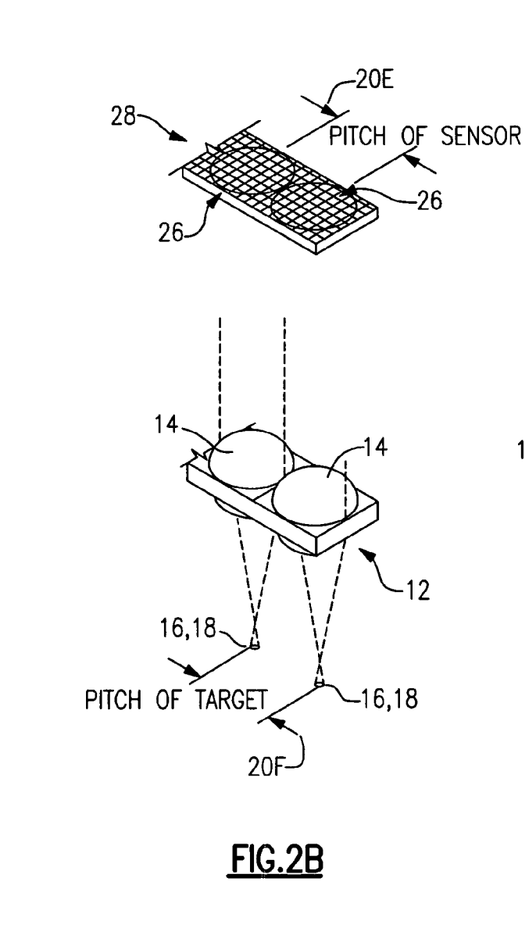
Figure 2C:
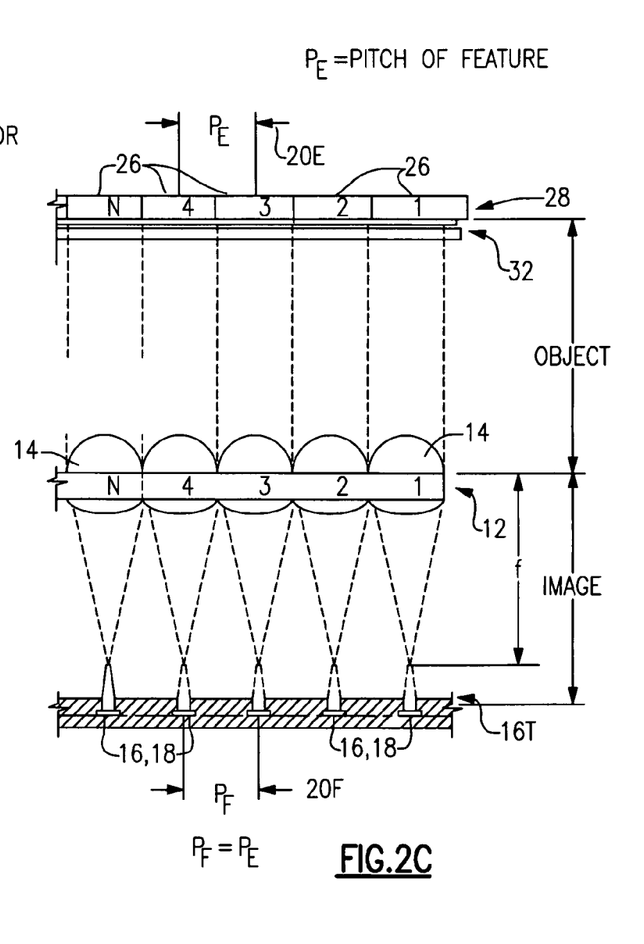
Figure 2D:
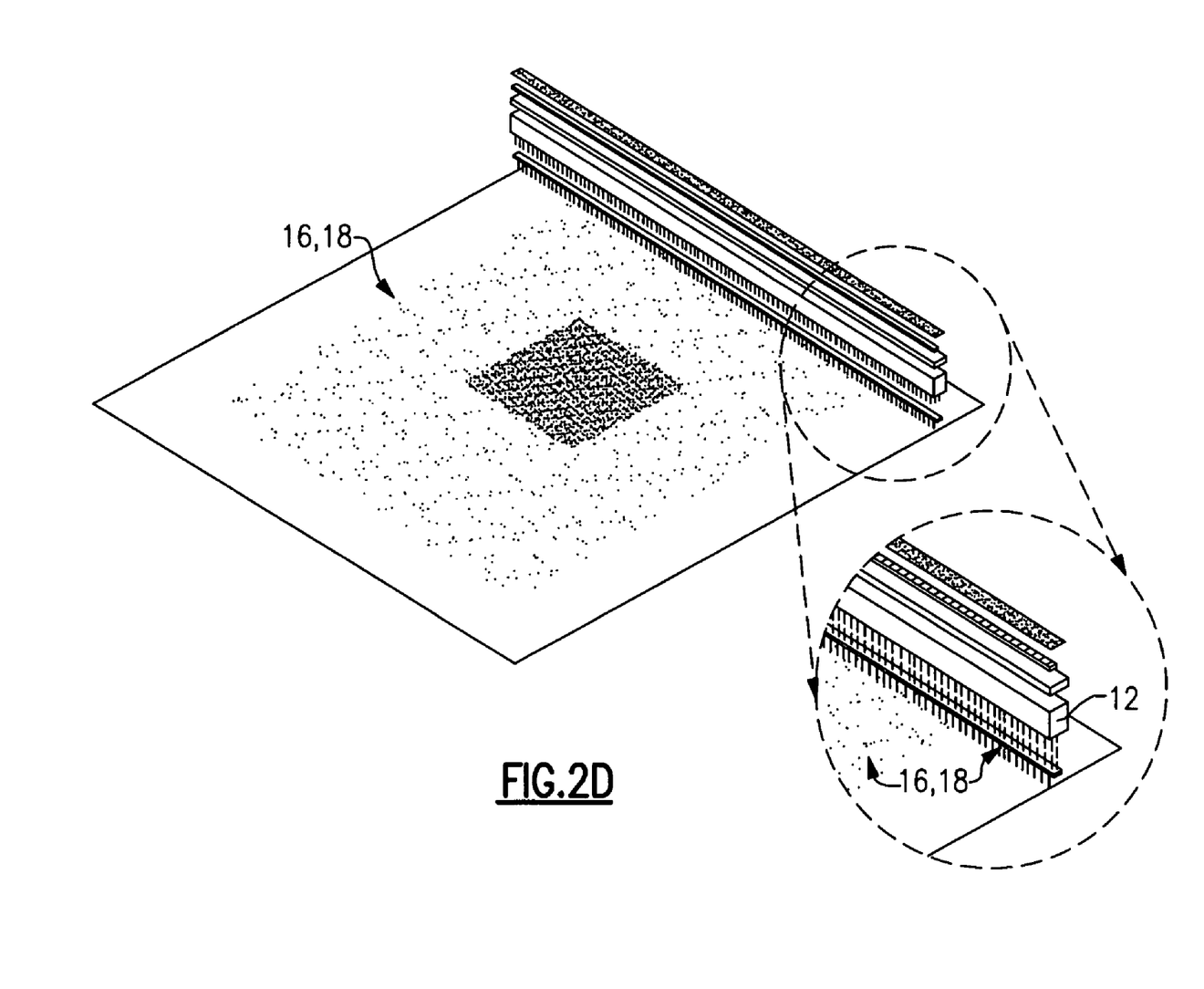

Therefore now considering further aspects of the method and systems of the present invention in further detail, and as illustrated in FIG. 2C, an imaging element array 28 may further include an illumination transformation element 32 in the input path from lenses 14 to imaging elements 26 of the imaging element array 28 to transform reflected illumination radiation from the target surface 16T and features 16 into radiation of a frequency that can be detected by the imaging elements 26. For example, the target surface 16T and features 16 may be illuminated with radiation in the infra-red (IR) or ultra-violet (UV) portions of the spectrum and the illumination transformation element may be a fluorescent plate that will convert the reflected IR or UV radiation into visible light that can be detected and imaged by the imaging elements 26.

Figure 3:
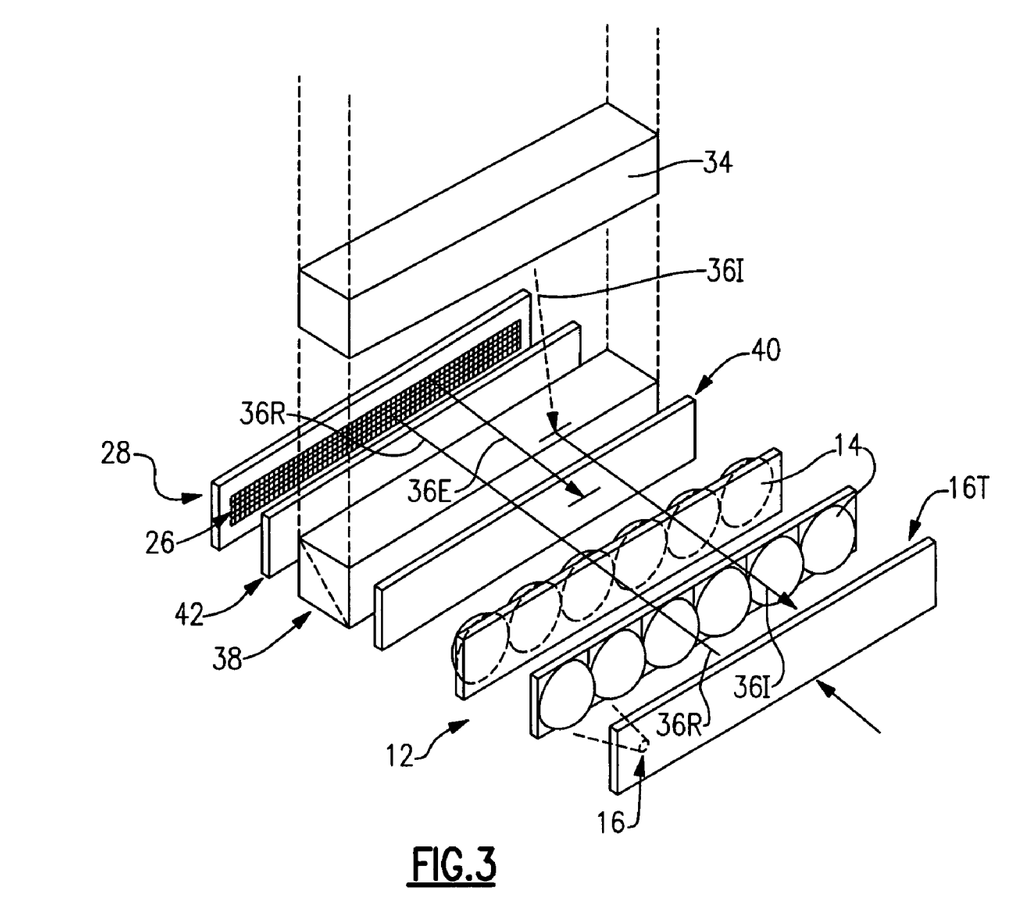
FIG. 3 is a diagrammatic illustration of a lens and camera system of the present invention with an illumination element and a filter elements.

Referring to FIG. 3, therein is illustrated an exemplary embodiment of the imaging system 10 that includes an illumination element 34 that generates illumination radiation 36I, such as IR, UV or visible radiation, that is directed onto the target surface 16T to illuminate the viewing areas 18 and features 16 thereon. As illustrated in FIG. 3, the illumination radiation 36I may be directed from illumination elements 34 and to target surface 16T by means of radiation redirection element 38, such as a beam splitter or equivalent element, with the reflected illumination radiation 36R returning from the target surface 16T and to the imaging array 28. through the lens array 12 and the alternate path through the radiation redirection element 38.

As also illustrated in FIG. 3, the imaging system 10 may further include a filtering element or elements 40 to narrow or limit the band width of the reflected imaging radiation 36R from the target surface 16T. Filtering element or elements 40 may also narrow, limit, reduce or suppress undesirable or unwanted radiation emissions 36E generated as a by-product of the imaging process, such as fluorescent emissions generated from either the imaging elements 26 or an illumination transformation element 32.

Lastly with respect to FIG. 3, the imaging system 10 may further include image transform optics 42 for to modify the characteristics of the image presented to the image array 28 as represented by reflected imaging radiation 36R to provide an image having desired characteristics. Image transform optics 42 may be comprised, for example, of hologrammic optical elements (HOEs) or diffractive optical elements (DOEs) or any other form of optical image manipulation elements and may be used, for example, to provide a better fill factor or increased quality of the image delivered to the imaging array 28.

Figure 4:
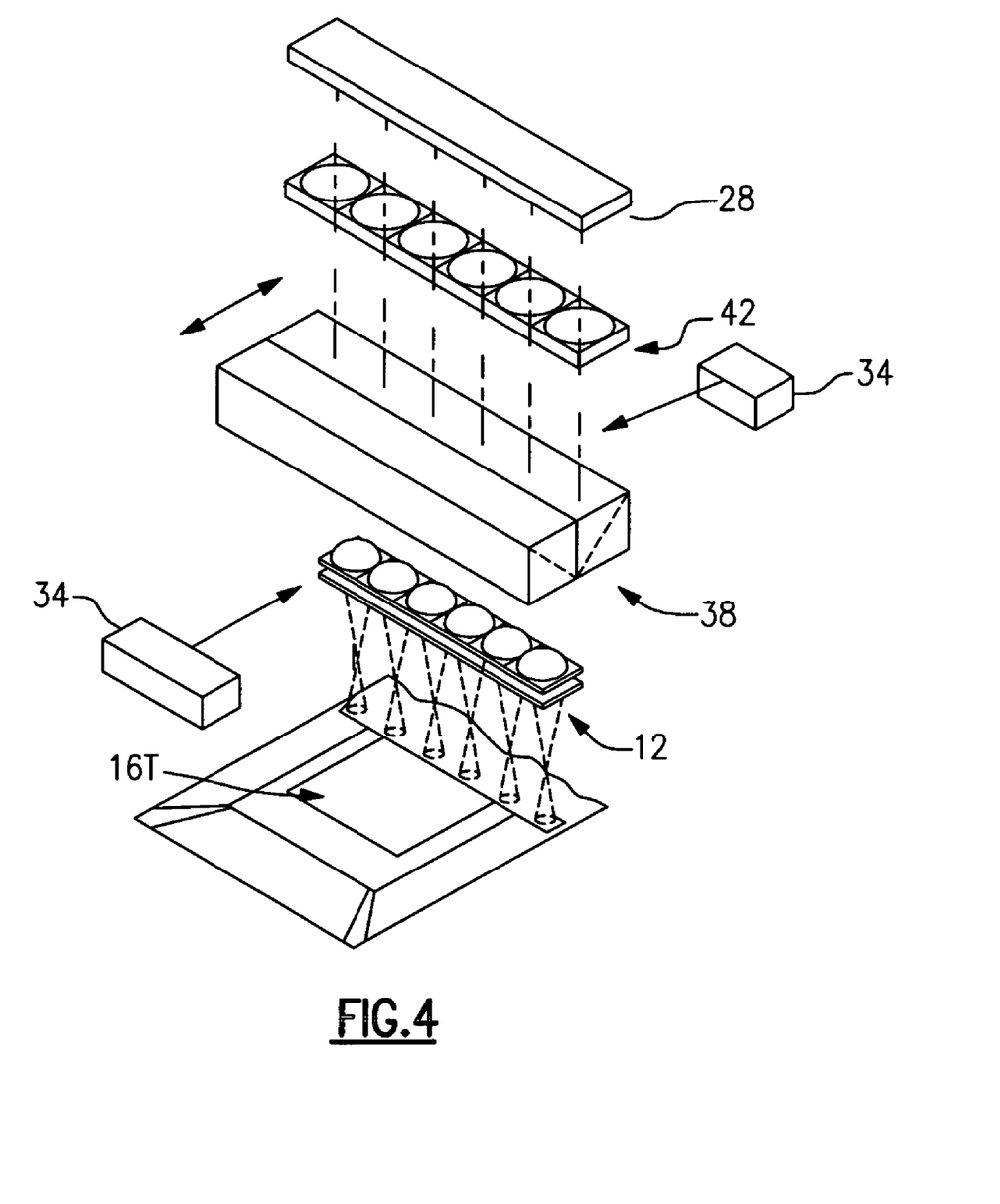
FIG. 4 is a diagrammatic representation of a lens and camera system of the present invention with plural selectable illumination sources.

FIG. 4 illustrates an imaging system 10 wherein the radiation redirection element 38 is comprised of a dual beam splitter that can be indexed relative to the optical path between the viewing areas 18 of the target surface 16T, the lens array 12 and the imaging array 28. The system 10 further includes two illumination elements 34 providing two or more illumination radiation 36I wavelengths with the wavelength of the illumination radiation 36I being determined by the index position of the dual beam splitters 38. As illustrated, one illumination element 34 may provide illumination radiation 36R in either or both of the infra-red and visual wavelengths and the other may provide illumination radiation 36I in the ultraviolet wavelengths, thereby allowing the illumination wavelength to be selected by indexing the corresponding beam splitter 38 into the illumination/image reflection beam path.

Figure 5:
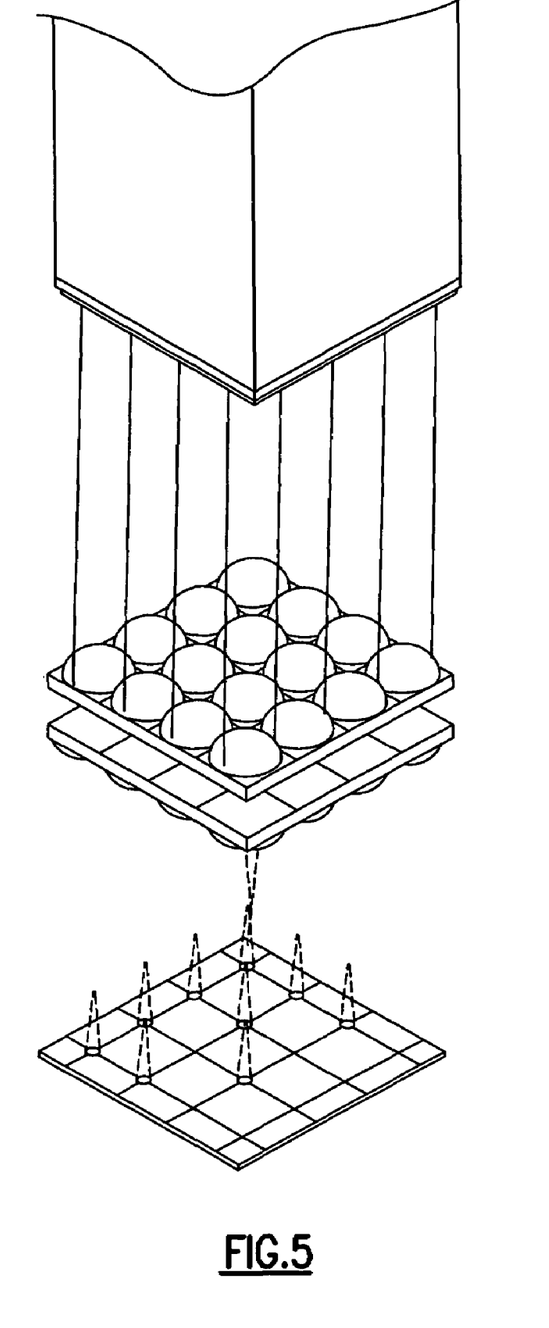
FIG. 5 is a diagrammatic representation of a lens and camera system with a two dimensional lens and camera element arrays.

FIG. 5 is an illustration of an imaging system 10 wherein lens array 12 is comprised of a two dimensional (2D) array of lenses 14 and wherein imaging array 28 is comprised of a corresponding two dimensional (2D) array of imaging elements 26. It will be appreciated that other elements of the system 10, such as illumination transformation element 32, filtering element or elements 40 and image transform optics 42 may likewise be expanded into two dimensional (2D) elements corresponding to the 2D arrays of imaging elements 26 and lenses 14.

Figure 6:
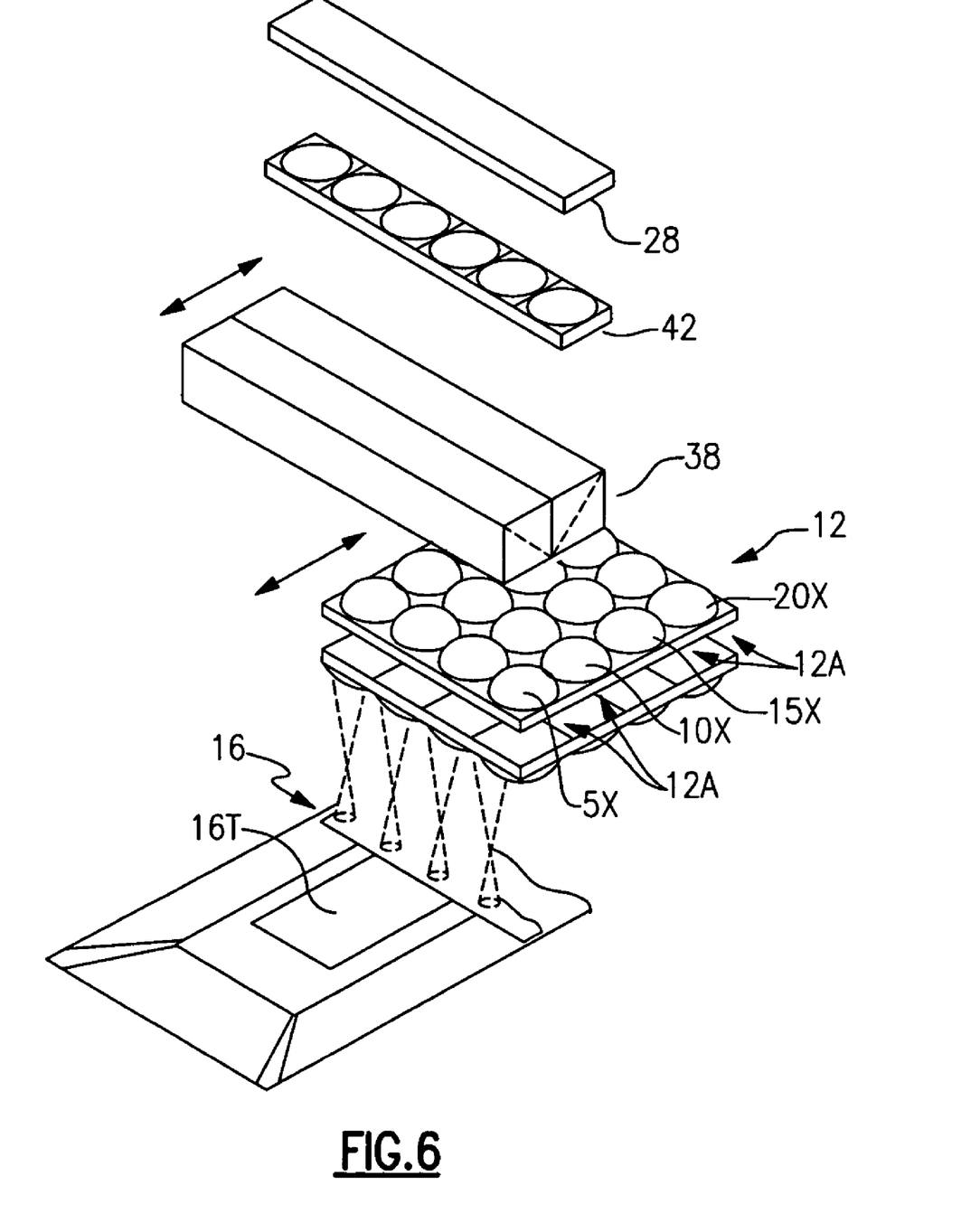
FIG. 6 is a diagrammatic representation of a lens and camera system with a two dimensional array of selectively indexable lenses of selectable magnification.

FIG. 6, in turn, is an illustration of an imaging system 10 wherein a two dimensional array 12 of lens elements 14 is comprised of a plurality of individual linear lens arrays 12A and wherein the lens elements 14 of each linear lens array 12A are of a specific imaging magnification. In the illustrative example, and for example, the magnification factors of the lens elements 14 of one linear lens array 12A may be 5×, the magnification factor of the lens elements of the next linear lens array 12A may be 10×, and so on through, for example, 15×, 20× and so on. The magnification factor of the lens array 12A selected for a given imaging process may then be selected from the available magnifications by indexing of the lens arrays 12A across the beam path of the reflected image radiation 36I. In yet another embodiment, the successive magnifications may be, for example, incremental steps, such as 5×, 6×, 7× and so on.

Figures 7A, 7B, 7C:
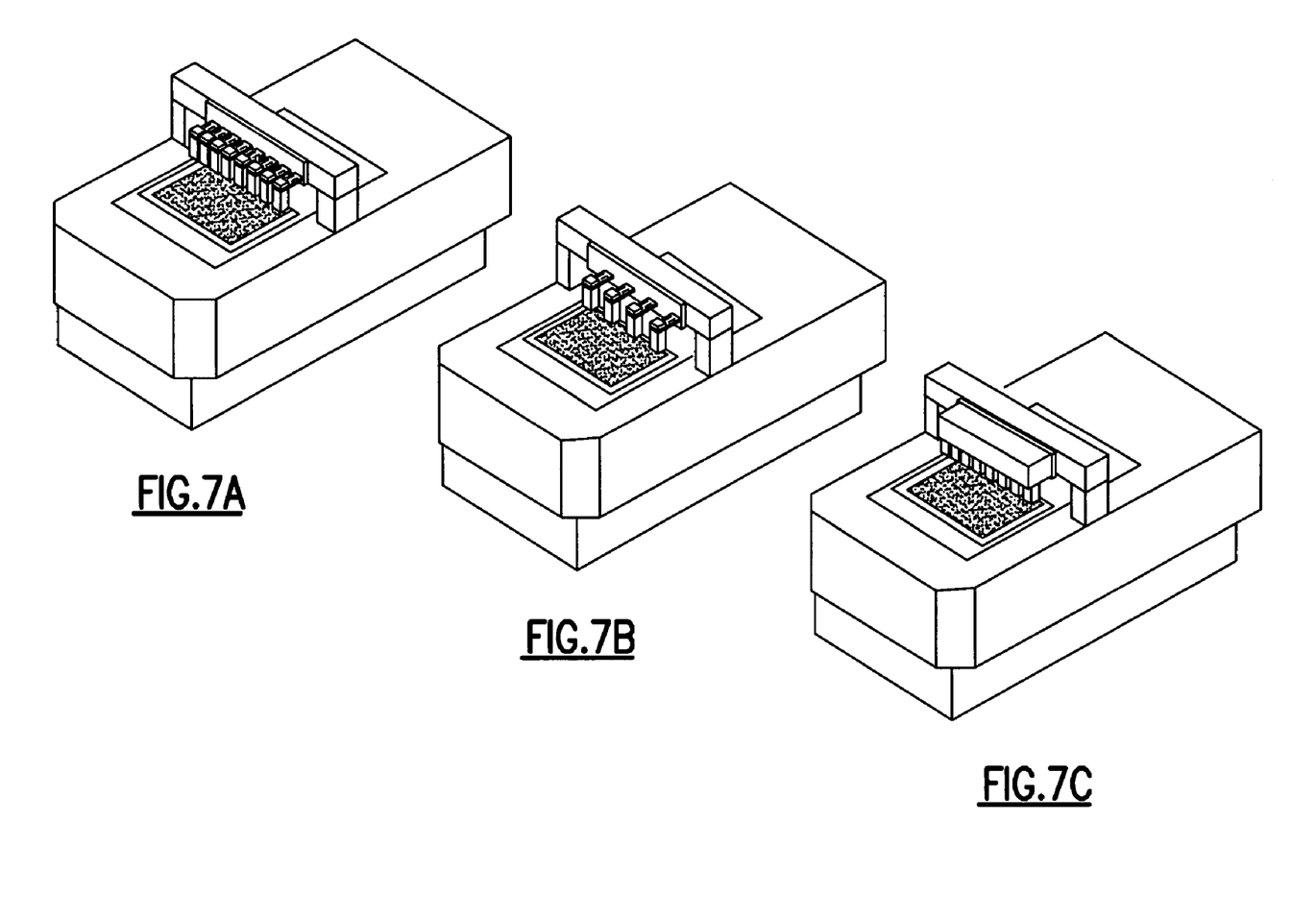
FIGS. 7A, 7B and 7C are diagrammatic representations of exemplary embodiments of the lens and camera system of the present invention.

FIGS. 7A, 7B and 7C illustrate camera 30 embodiments for systems 10 using, respectively, an imaging array using 8 camera devices 30, 4 camera devices 30 and a single monolithic array camera device 30, each of which will provide a different throughput rate. It will also be appreciated that a system 10 may employ staggered arrays of camera devices 30, depending upon the arrangement of features 16 and viewing areas 18 on, for example, a PCB, and specific imaging needs.

Figure 8:
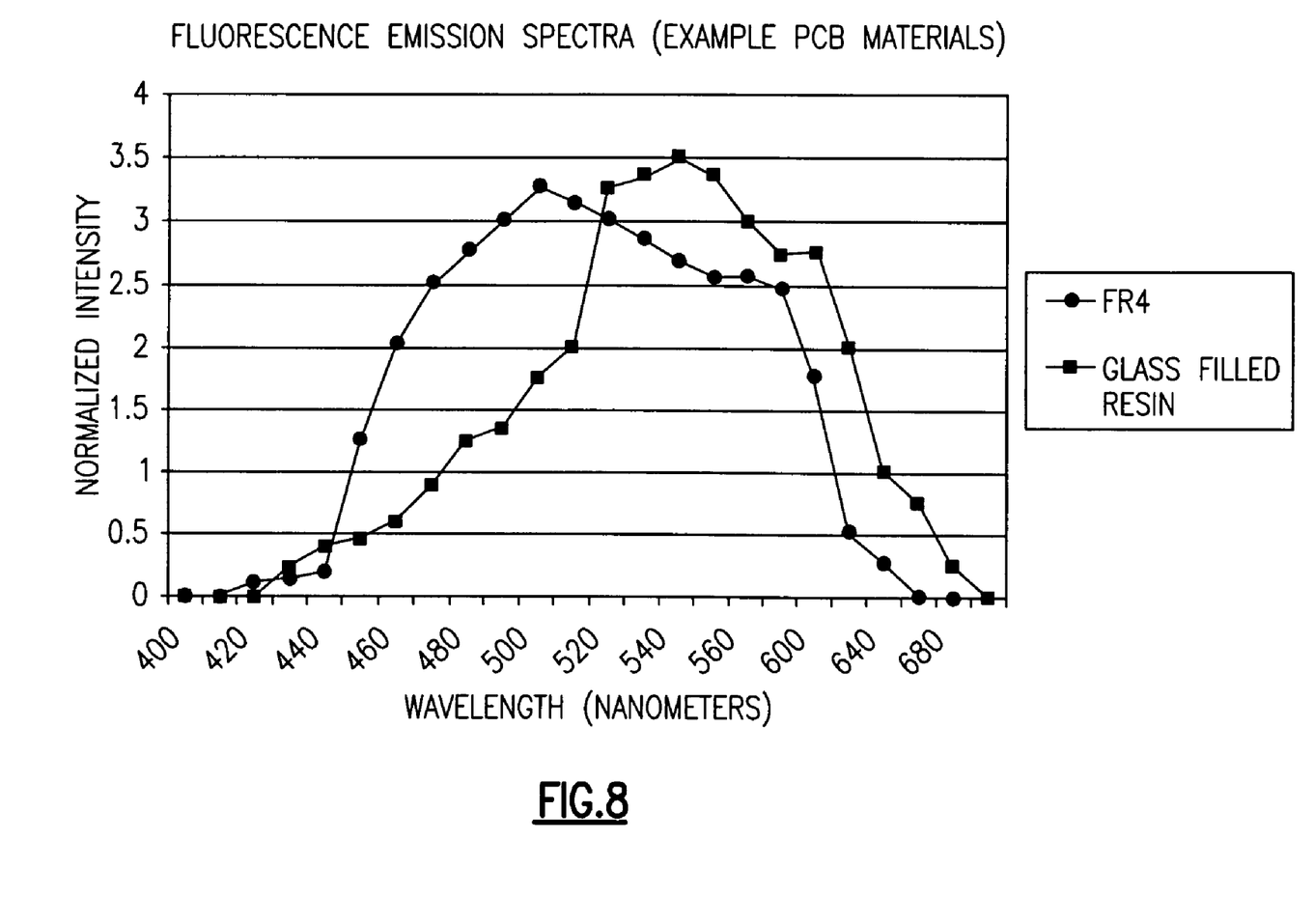
FIGS. 8 and 9 are representations of the fluorescent emission and reflectivity of various PCB materials under different wavelengths of illumination.
Figure 9:
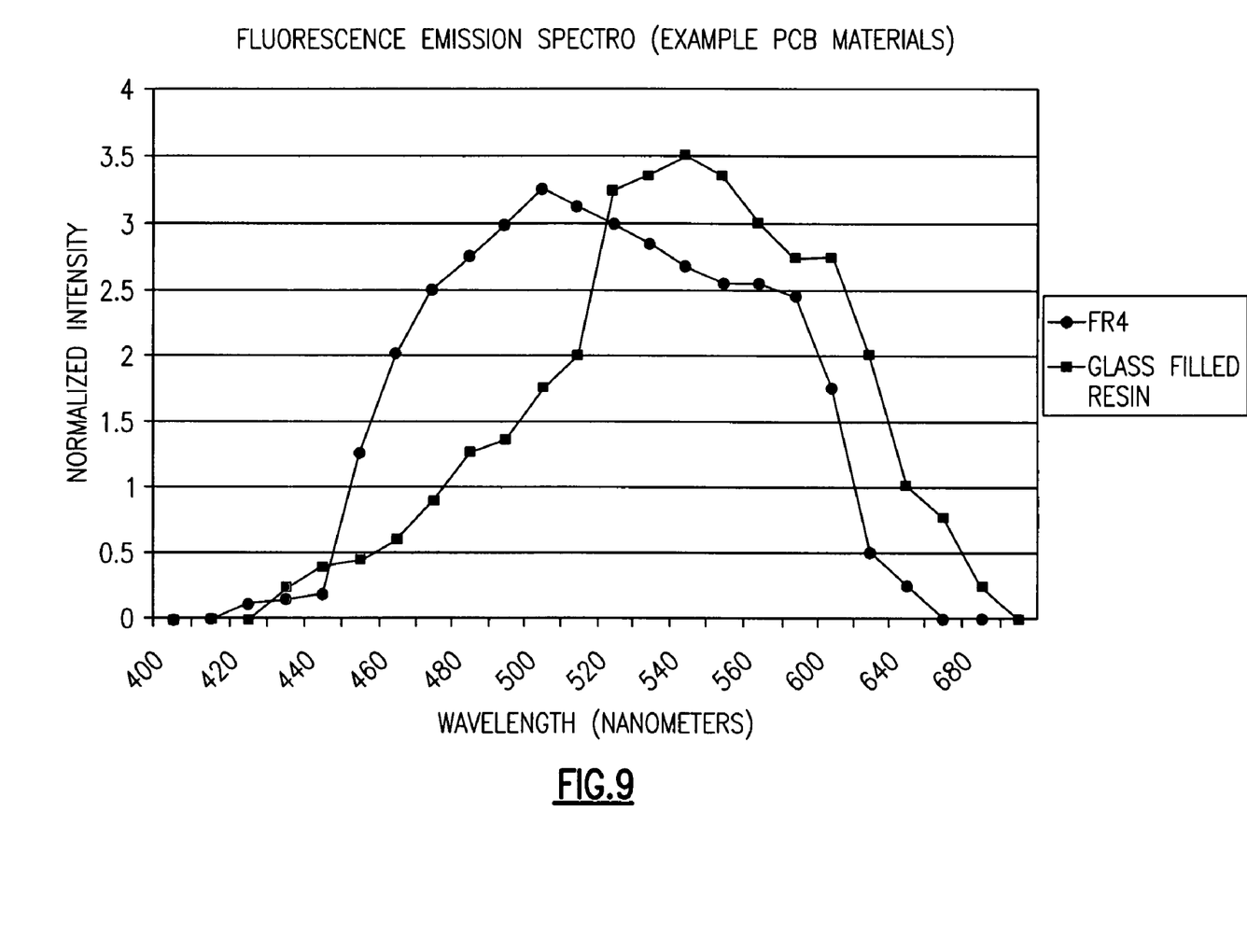

Lastly with regard to the above discussions, FIG. 8 presents data regarding the fluorescent emission of various PCB materials when illuminated with a specific band of ultraviolet illumination, and FIG. 9 presents data regarding the reflectivity of various metals used as PCB conductor levels when illuminated by infrared, visible light and ultraviolet illumination sources.

Figure 10:
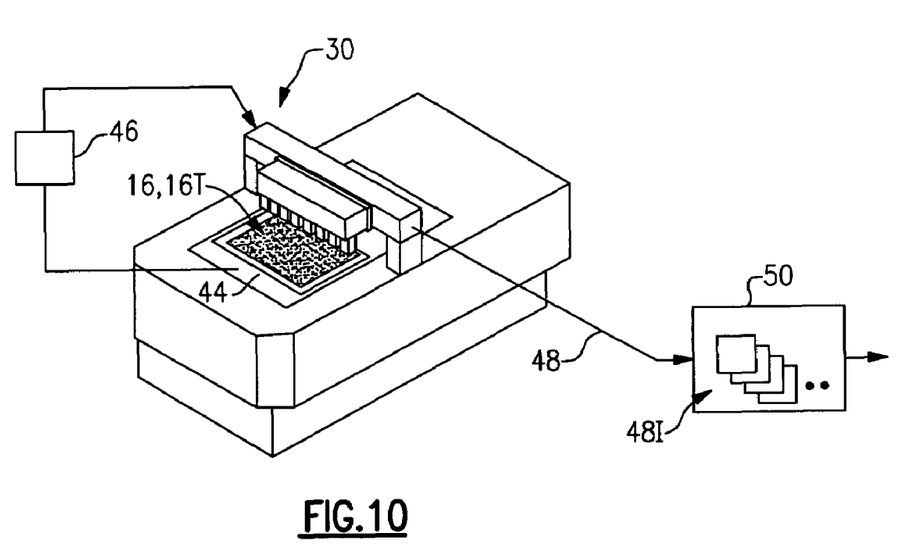
FIG. 10 is a diagrammatic illustration of time delay and integration scanning for processing images of features of a printed circuit board; and, FIGS. 11A and 11B are diagrammatic illustrations of exemplary embodiments of the lens array incorporating baffles for reduction of cross-talk between lenses, particularly with flood illumination.

Next considering the camera device 30 and methods of image scanning and processing, a presently preferred embodiment of an imaging system 10 employs a CCD camera with Time Delay and Integration (TDI) scanning wherein TDI methods employ the accumulation of multiple exposures or scans of a given moving object. In TDI methods the motion of the object is synchronized with the scanning or imaging to ensure a "crisp" high resolution image and the accumulation of multiple exposures effectively increases the integration time over which incident light from the image, that is, the reflected image radiation from a given target area or feature is collected. As illustrated diagrammatically in FIG. 10 with respect to the embodiment illustrated in FIG. 7C, a PCB having a target surface 16T bearing features 16 of interest is mounted onto a moveable web 44 that incrementally moves the target surface 16T under the lens array 12 of the camera device 30 along one or two axes, thereby progressively and incrementally moving features 16 through viewing areas 18 of the camera device 30. Camera device 30 thereby captures successive images of the features 16 as they pass through the viewing areas 18. As indicated, the motion of web 44, and thus of target surface 16T and the features 16 thereon, is synchronized with camera device 30 by a synchronization control 46, so that camera device 30 captures successive images 48 of target surface 16T and the features 16. The successively captured images 48 are accumulated, that is, effectively time integrated, in an image processing unit 50 and the resulting integrated images 48I are then inspected, typically by or with the aid of an image inspection process, to provide outputs representing the results of the inspection of the PCB.

The advantages of TDI methods are, first, that with effectively increased image integration time the speed of scanning of the target surface 16T and features 16 or of the camera device 30 can be increased, thereby increasing the throughput of the system. In addition, the effectively longer image integration time allow the target surface 16T and features 16 to be illuminated with lower light levels, such as high-frequency AC or even LED lighting, instead of high-powered, high-cost, high-temperature halogen lighting with DC power. This in turn reduces system complexity and costs, including maintenance costs. Also, TDI processing effectively averages out fluctuations in light intensity, so that DC illumination sources are note required, which can justify the increased cost of a TDI sensor versus the cost of using DC regulated light source and a line scan image sensor.

TDI methods do require more care in the synchronization and alignment of the camera device 30 and the features 16 of interest, but these requirements are readily met. In addition, it must be noted that TDI sensor camera device and processing can readily accommodate some degree of translational or rotational misalignment or both, such as up to one pixel of less across the length of a TDI sensor, without negative effect on the image quality. For example, in most applications a 96-stage TDI device 30 can comfortably accommodate a 24% velocity mismatch between the inspection web, that is, the target surface 16T, and the imaging elements. This is not difficult to achieve using a web-mounted encoder to supply a synchronization signal to the camera device 30, even with variable or changeable speed webs and this approach is often used in successful applications.

In summary, a presently preferred embodiment of the invention has the following characteristics and specifications:

Lens Diameter: 300 $\mu\mu m$ to 600 $\mu\mu m$ Diameter;

Lens Pitch: 150 $\mu\mu m$ to 600 $\mu\mu m$ (Linear & Array and Staggered Array configuration);

Lens Integrated Aperture: Cross Talk Aperture Array Integrated Into Lens Array;

Working Distance: >350 $\mu\mu m$ (Optimum between 500 $\mu\mu m$ to 1000 $\mu\mu m$);

Numerical Aperture: >0.1 NA;

CCD Array Size: 8192 pixels×96 pixels (Linear TDI);

Optimum CCD Array Size: 1024 pixels×1024 pixels (Array);

Pixel Size: 7 $\mu\mu m$×7 $\mu\mu m$ to 12 $\mu\mu m$×12 $\mu\mu m$ Range (7 $\mu\mu m$×7 $\mu\mu m$ Optimum);

Filter: Low pass filter (Specific wavelength band between 480 nm to 600 nm);

Coaxial illumination: UV, IR and Visible Capable (Optimum illumination Range 350 nm to 500 nm);

Fluorescence Wavelength Detected: 480 nm to 580 nm; and

Camera Type: CCD TDI (Time Delay and Integration) High Sensitivity.

Figure 11A:
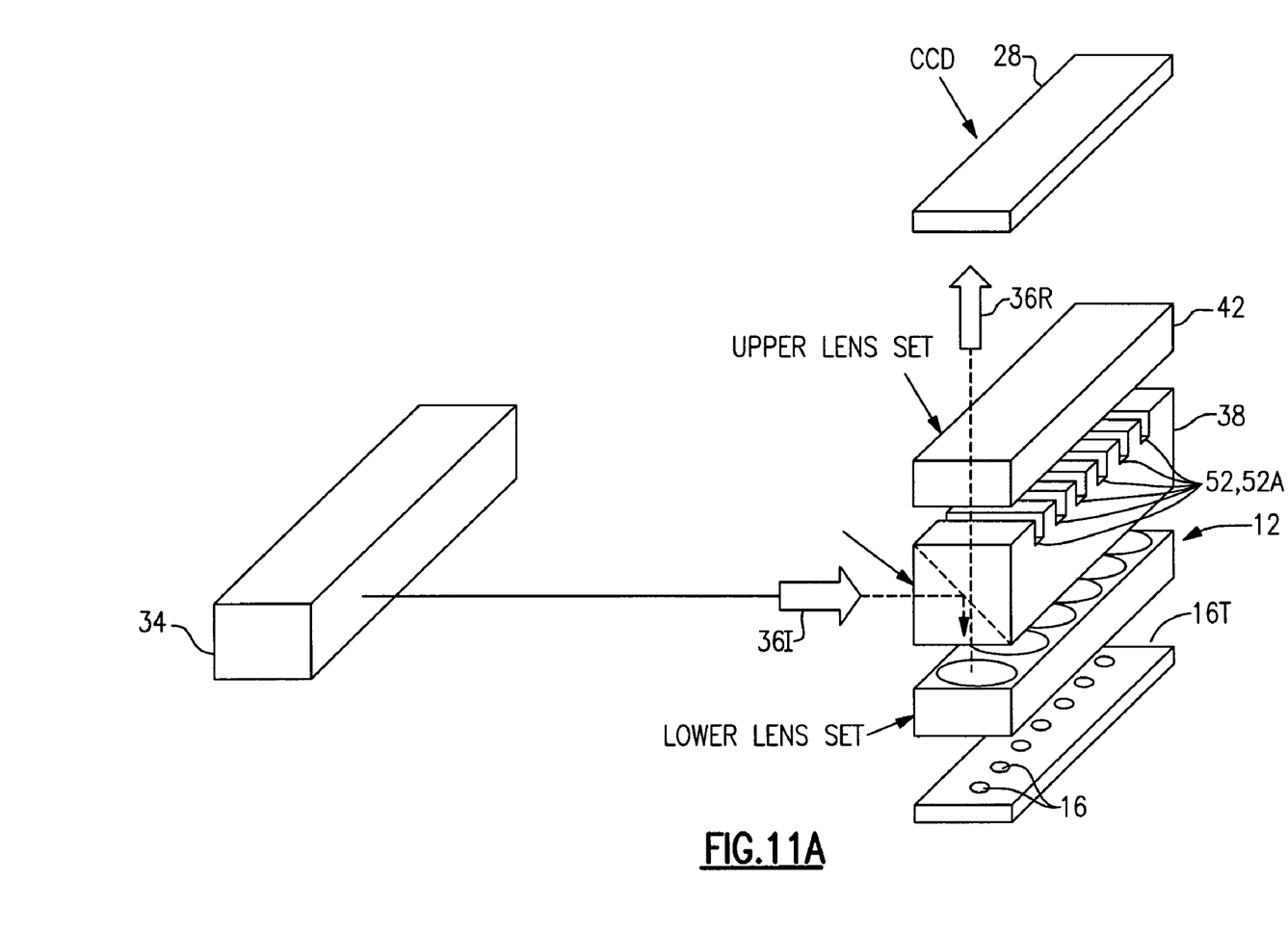
Figure 11B:
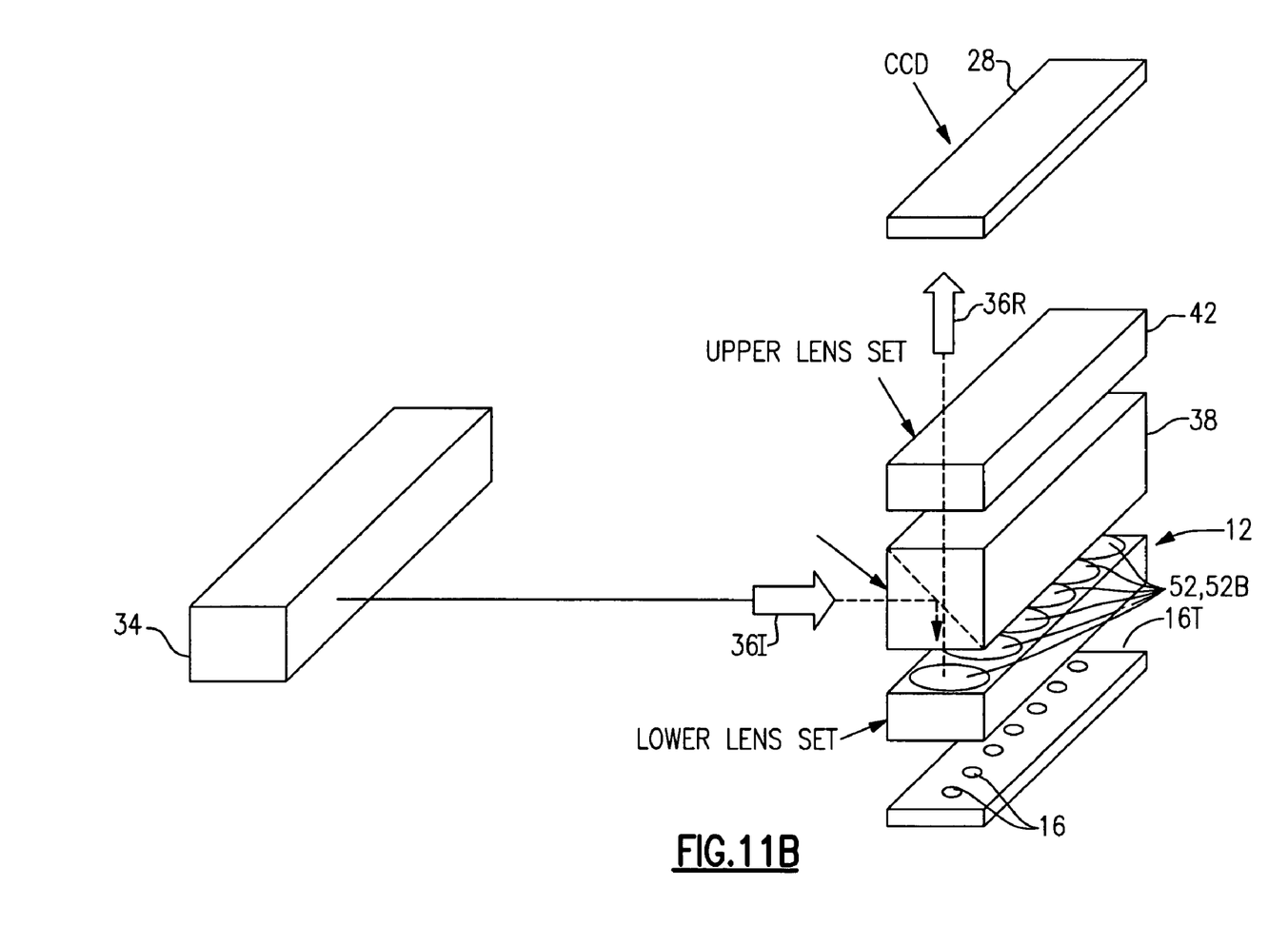

Lastly considering certain further and alternative embodiments of the above described invention, FIGS. 11A and 11B are diagrammatic illustrations of exemplary embodiments of the lens array incorporating baffles for reduction of cross-talk between lenses, particularly with flood illumination of target surface 16T and features 16. As described above and as illustrated in FIGS. 11A and 11B, target surface 16T and features 16 may be illuminated by means of a an illumination element 34 that generates illumination radiation 36I, such as IR, UV or visible radiation, that is directed onto the target surface 16T to illuminate the viewing areas 18 and features 16 thereon. As illustrated in FIG. 3 and in FIGS. 11a and 11B, the illumination radiation 36I may be directed from illumination element 34 and to target surface 16T by means of radiation redirection element 38, such as a beam splitter or equivalent element, with the reflected illumination radiation 36R returning from the target surface 16T and to the imaging array 28. through the lens array 12 and the alternate path through the radiation redirection element 38.

Illumination element 34 is typically a "flood" type source, that is, it generates a broad band or beam of illumination radiation 36I across the entire width and height of the receiving surface of beam splitter 38 and thus most or all of the length and width of target surface 16T rather than generating numbers individual beams to illuminate the individual fields of view 18 of lenses 14. The general rather than focused illumination of target surface 16T, spreading of the reflected illumination radiation 36R from target surface 16T and through lenses 14, and random scattering and local reflections, may result in "crosstalk" or "spill-over" between the field of view 18 images transmitted through lenses 14, and thus degradation of the images at imaging array 28.

For this reason, the imaging systems 10 illustrated in FIGS. 11A and 11B incorporate baffles 52 to effectively block crosstalk or spill-over radiation between the images arriving at imaging element array 28. In the embodiment illustrated in FIG. 11A, the baffles 52 are implemented in beam splitter 38 as three dimensional baffles 52A wherein baffles 52A are formed, for example, by slits cut into the upper surface of beam splitter 38, that is, the surface of beam splitter 38 from which reflected illumination radiation 36R is transmitted onward to imaging element array 28. In a typical implementation, and for example, the slits forming baffles 52A may be 50 μm wide by 100 μm deep and may be formed by use of a wafer dicing saw. In the implementation illustrated in FIG. 11B, baffles 52 are formed as baffles 52B formed of ring trenches around each of the lenses 14 of lens array 12 and may be formed, for example, by laser etching after the molding of the lens array 12 or by molding the ring trenches into the lens array 12 during casting of the lens array 12.

In conclusion, while the invention has been particularly shown and described with reference to preferred embodiments of the apparatus and methods thereof, it will be also understood by those of ordinary skill in the art that various changes, variations and modifications in form, details and implementation may be made therein without departing from the spirit and scope of the invention as defined by the appended claims.

What is claimed is:

1. An imaging system for inspecting features located at a known inter-feature pitch on portions of a target surface, comprising:
    a lens array having a plurality of lenses,
        the lenses of the lens array having
            an inter-lens pitch and an inter-field of view pitch corresponding to the inter-feature pitch, and
    an array of imaging elements having an inter-element pitch corresponding to the inter-feature pitch, whereby the imaging system images only field of view areas of the target surface containing features.

2. The imaging system for inspecting features located at a known inter-feature pitch on portions of a target surface of claim 1, further comprising:
    an illumination transformation element located between the lens array and the imaging element array for transforming reflected imaging radiation from the field of view areas of the target surface into visible light for imaging by the imaging elements.

3. The imaging system for inspecting features located at a known inter-feature pitch on portions of a target surface of claim 2, further comprising:
    a filtering element located between the lens array and the imaging array to limit wavelengths of at least one of reflected imaging radiation reflected from the target surface and radiation emitted by the illumination transformation element in transforming the reflected imaging radiation from the target surface.

4. The imaging system for inspecting features located at a known inter-feature pitch on portions of a target surface of claim 1, further comprising:
    an image transformation optical element for modifying the characteristics of an image represented by the reflected imaging radiation from the target surface.

5. The imaging system for inspecting features located at a known inter-feature pitch on portions of a target surface of claim 1, further comprising:
    an illumination element for generating illumination radiation for illuminating the field of view areas of the target surface, and
    a radiation redirection element located between the imaging array and lens array to receive the illumination radiation from the illumination element and direct the illumination radiation to the target surface and to pass reflected imaging radiation from the target surface to the imaging array.

6. The imaging system for inspecting features located at a known inter-feature pitch on portions of a target surface of claim 1, further comprising:
    a plurality of illumination elements for generating illumination radiation corresponding wavelengths for illuminating the field of view areas of the target surface,
    a plurality of radiation redirection elements located between the imaging array and lens array, each radiation redirection element receiving the illumination radiation from at least one corresponding illumination element and directing the received illumination radiation to the target surface and passing reflected imaging radiation of a corresponding wavelength from the target surface to the imaging array.

7. The imaging system for inspecting features located at a known inter-feature pitch on portions of a target surface of claim 1, wherein:
    the lens and imaging element arrays are two dimensional arrays imaging a corresponding two dimensional array of viewing areas of the target surface.

8. The imaging system for inspecting features located at a known inter-feature pitch on portions of a target surface of claim 1, wherein:
    the lens array is a two dimensional array of rows of lenses wherein
        each row of lenses contains lenses of a single magnification and successive rows of lenses contain lenses of different magnifications, and
    the lens array is selectively indexed by rows row to select a single row of lenses as a linear array of lenses at a corresponding magnification for imaging of the features.

9. The imaging system for inspecting features located at a known inter-feature pitch on portions of a target surface of claim 1, further comprising:
    a plurality of cross-talk baffles in an optical path between the lenses of the lens array and the array of imaging elements.

10. The imaging system for inspecting features located at a known inter-feature pitch on portions of a target surface of claim 9 wherein:
    each cross talk-baffle is formed by a ring trench surrounding a corresponding lens of the lens array.

11. The imaging system for inspecting features located at a known inter-feature pitch on portions of a target surface of claim 5, further comprising:
    a plurality of cross-talk baffles in an optical path between the lenses of the lens array and the array of imaging elements.

12. The imaging system for inspecting features located at a known inter-feature pitch on portions of a target surface of claim 11, wherein:
    each cross-baffle is formed of a slit in the radiation redirection element, each slit being located between adjacent optical paths between corresponding adjacent lenses of the lens array and the array of imaging elements.

* * * * *